United States Patent
Ross et al.

(10) Patent No.: US 6,663,644 B1
(45) Date of Patent: *Dec. 16, 2003

(54) CUTTING BLADE ASSEMBLY FOR A MICROKERATOME

(75) Inventors: Rod Ross, Mission Viejo, CA (US); Gregg Hughes, Mission Viejo, CA (US); Mark Moyer, San Marcos, CA (US); James Robert Dennewill, Cerritos, CA (US)

(73) Assignee: Med-Logics, Inc., Laguna Niguel, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/585,566

(22) Filed: Jun. 2, 2000

(51) Int. Cl.$^7$ .................................................. A61F 9/00
(52) U.S. Cl. .......................................... 606/166; 604/22
(58) Field of Search ............................ 606/1, 166, 167, 606/170, 172, 169, 180

(56) References Cited

U.S. PATENT DOCUMENTS

| | | | |
|---|---|---|---|
| 1,841,968 A | 1/1932 | Lowry | |
| 1,847,658 A | 3/1932 | Lasker | |
| 2,070,281 A | 2/1937 | Leggiadro | |
| 2,457,772 A | 12/1948 | Brown | |
| 2,480,737 A | 8/1949 | Jayle | |

(List continued on next page.)

FOREIGN PATENT DOCUMENTS

| | | |
|---|---|---|
| DE | 25 47 185 | 4/1977 |
| EP | 1033 120 A2 | 6/2000 |
| FR | 2 549 727 | 7/1963 |

OTHER PUBLICATIONS

Steinway Instrument Company Inc., The Steinway/Barraquer in–Situ Microkeratome Set.
Brochure, Site TXR Systems, Site Mycrosurgical Systems, Inc., Horsham, Pennsylvania.
Marshall M. Parks, "Intracapsular Aspiration" article, pp. 59–74.
Van Oldenborgh, "Correction of late operative complications by means of a suction cutter", Opthal. Soc. U.K. (1980), 100, 219, pp. 219–221.
Helfgott, M.D. "A System for Variable Aspiration of Material Dissected from the Posterior Chamber", Ophthalmic Surgery, vol. 15, Jun. 1984, pp. 529–350.
Coopervision Brochure on Cavitron/Kelman Model 6500 E.I.S. and Model 7500, 6 pages.
Surgical Design Brochure on "The Ocusystem", 1 page.
Coopervision Brochure on "Cavitorn/Kelman Phaco–Emulsifier Aspirator Model 8001", 2 pages.
Coopervision Brochure on Cavitron/Kelman Phaco–Emulsifier Aspirator Model 9001, 6 pages.
Greishaber of Switzerland Brochure on "MPC, The Membrane Peeler Cutter", 5 pages.
Micro–Vit Vitrectomy System Product Brochure and Instruction Manual.

(List continued on next page.)

Primary Examiner—Michael J. Milano
Assistant Examiner—Victor Nguyen
(74) Attorney, Agent, or Firm—Irell & Manella LLP

(57) ABSTRACT

A blade assembly that can be assembled into a microkeratome which is used to cut a cornea. The blade assembly is constructed in a manner that minimizes the tolerance of the cutting depth into the cornea. The blade assembly includes a blade holder that can be pressed onto a blade. The relative position of the blade holder can be calibrated to control the distance between a reference surface of the blade holder and the cutting edge of the blade. This distance defines the cutting depth of the blade. The blade holder is coupled to the blade with an interference fit that both secures the holder while providing for calibration of the assembly.

6 Claims, 5 Drawing Sheets

U.S. PATENT DOCUMENTS

| | | |
|---|---|---|
| RE23,496 E | 5/1952 | Seeler |
| 2,708,437 A | 5/1955 | Hutchins |
| 2,824,455 A | 2/1958 | Ristow et al. |
| 3,033,196 A | 5/1962 | Hay |
| 3,252,623 A | 5/1966 | Corbin et al. |
| 3,266,494 A | 8/1966 | Brownrigg et al. |
| 3,308,828 A | 3/1967 | Pippin |
| 3,399,677 A | 9/1968 | Gould et al. |
| 3,511,162 A | 5/1970 | Truhan |
| 3,561,429 A | 2/1971 | Jewett |
| 3,583,403 A | 6/1971 | Pohl |
| 3,589,363 A | 6/1971 | Banko |
| 3,624,821 A | 11/1971 | Henderson |
| 3,693,613 A | 9/1972 | Kelman |
| 3,723,030 A | 3/1973 | Gelfand |
| 3,752,161 A | 8/1973 | Bent |
| 3,763,862 A | 10/1973 | Spieth |
| 3,812,855 A | 5/1974 | Banko |
| 3,815,604 A | 6/1974 | O'Malley et al. |
| 3,841,799 A | 10/1974 | Spinosa et al. |
| 3,842,839 A | 10/1974 | Malis et al. |
| 3,882,872 A | 5/1975 | Douvas et al. |
| 3,884,238 A | 5/1975 | O'Malley et al. |
| 3,899,829 A | 8/1975 | Storm et al. |
| 3,903,881 A | 9/1975 | Weigl |
| 3,913,584 A | 10/1975 | Walchle et al. |
| 3,920,014 A | 11/1975 | Banko |
| 3,930,505 A | 1/1976 | Wallach |
| 3,977,425 A | 8/1976 | Hayashida |
| 3,982,539 A | 9/1976 | Muriot |
| 3,983,474 A | 9/1976 | Kuipers |
| 3,986,512 A | 10/1976 | Walliser |
| 4,004,590 A | 1/1977 | Muriot |
| 4,011,869 A | 3/1977 | Seiler, Jr. |
| 4,034,712 A | 7/1977 | Duncan |
| 4,043,342 A | 8/1977 | Morrison, Jr. |
| 4,108,182 A | 8/1978 | Hartman et al. |
| 4,135,515 A | 1/1979 | Muriot |
| 4,137,920 A | 2/1979 | Bonnet |
| 4,168,707 A | 9/1979 | Douvas et al. |
| 4,173,980 A | 11/1979 | Curtin |
| 4,178,707 A | 12/1979 | Littlefield |
| 4,204,328 A | 5/1980 | Kutner |
| 4,205,682 A | 6/1980 | Crock et al. |
| 4,210,146 A | 7/1980 | Banko |
| 4,217,993 A | 8/1980 | Jess et al. |
| 4,223,676 A | 9/1980 | Wuchinich et al. |
| 4,245,815 A | 1/1981 | Willis |
| 4,246,902 A | 1/1981 | Martinez |
| 4,274,411 A | 6/1981 | Dotson, Jr. |
| 4,301,802 A | 11/1981 | Poler |
| 4,304,262 A | 12/1981 | Icking |
| 4,308,385 A | 12/1981 | Goorden |
| 4,308,835 A | 1/1982 | Abbey |
| 4,314,560 A | 2/1982 | Helfgott et al. |
| 4,319,899 A | 3/1982 | Marsh |
| 4,320,761 A | 3/1982 | Haddad |
| 4,344,784 A | 8/1982 | Deckas et al. |
| 4,354,838 A | 10/1982 | Hoyer et al. |
| 4,395,258 A | 7/1983 | Wang et al. |
| 4,396,386 A | 8/1983 | Kurtz et al. |
| 4,427,427 A | 1/1984 | DeVecchi |
| 4,428,748 A | 1/1984 | Peyman et al. |
| 4,429,696 A | 2/1984 | Hanna |
| 4,445,517 A | 5/1984 | Feild |
| 4,474,411 A | 10/1984 | Peters et al. |
| 4,475,904 A | 10/1984 | Wang |
| 4,476,862 A | 10/1984 | Pao |
| 4,479,717 A | 10/1984 | Cornillault |
| 4,481,948 A | 11/1984 | Sole |
| 4,493,695 A | 1/1985 | Cook |
| 4,493,698 A | 1/1985 | Wang et al. |
| 4,522,371 A | 6/1985 | Fox et al. |
| 4,523,911 A | 6/1985 | Braetsch et al. |
| 4,524,948 A | 6/1985 | Hall |
| 4,530,357 A | 7/1985 | Pawloski et al. |
| 4,531,934 A | 7/1985 | Kossovsky et al. |
| 4,540,406 A | 9/1985 | Miles |
| 4,555,645 A | 11/1985 | Atkinson |
| 4,560,395 A | 12/1985 | Davis |
| 4,589,414 A | 5/1986 | Yoshida et al. |
| 4,598,729 A | 7/1986 | Naito et al. |
| 4,647,209 A | 3/1987 | Neukomm et al. |
| 4,660,556 A | 4/1987 | Swinger et al. |
| 4,660,970 A | 4/1987 | Ferrano |
| 4,662,370 A | 5/1987 | Hoffmann et al. |
| 4,665,914 A | 5/1987 | Tanne |
| 4,674,499 A | 6/1987 | Pao |
| 4,674,503 A | 6/1987 | Peyman et al. |
| 4,678,459 A | 7/1987 | Onik et al. |
| 4,688,570 A | 8/1987 | Kramer et al. |
| 4,690,099 A | 9/1987 | Gregan et al. |
| 4,701,049 A | 10/1987 | Beckmann et al. |
| 4,705,395 A | 11/1987 | Hageniers |
| 4,706,687 A | 11/1987 | Rogers et al. |
| 4,723,545 A | 2/1988 | Nixon et al. |
| 4,743,770 A | 5/1988 | Lee |
| 4,757,814 A | 7/1988 | Wang et al. |
| 4,767,403 A | 8/1988 | Hodge |
| 4,768,506 A | 9/1988 | Parker et al. |
| 4,770,654 A | 9/1988 | Rogers et al. |
| 4,782,239 A | 11/1988 | Hirose et al. |
| 4,782,849 A | 11/1988 | Hodge |
| 4,791,934 A | 12/1988 | Brunnett |
| 4,805,615 A | 2/1989 | Carol |
| 4,805,616 A | 2/1989 | Pao |
| 4,807,623 A | 2/1989 | Lieberman |
| 4,819,635 A | 4/1989 | Shapiro |
| 4,825,091 A | 4/1989 | Breyer et al. |
| 4,828,306 A | 5/1989 | Blatt |
| 4,830,047 A | 5/1989 | Hodge |
| 4,837,857 A | 6/1989 | Scheller et al. |
| 4,838,281 A | 6/1989 | Rogers et al. |
| 4,840,175 A | 6/1989 | Peyman |
| 4,865,033 A | 9/1989 | Krumeich et al. |
| 4,884,570 A | 12/1989 | Krumeich et al. |
| 4,886,085 A | 12/1989 | Miller |
| 4,903,695 A | 2/1990 | Warner et al. |
| 4,909,815 A | 3/1990 | Meyer |
| RE33,250 E | 7/1990 | Cook |
| 4,943,289 A | 7/1990 | Goode et al. |
| 4,965,417 A | 10/1990 | Massie |
| 4,988,347 A | 1/1991 | Goode et al. |
| 4,997,437 A | 3/1991 | Grieshaber |
| 5,011,482 A | 4/1991 | Goode et al. |
| 5,013,310 A | 5/1991 | Goode et al. |
| 5,019,076 A | 5/1991 | Yamanashi et al. |
| 5,059,204 A | 10/1991 | Lawson et al. |
| 5,083,558 A | 1/1992 | Thomas et al. |
| 5,106,364 A | 4/1992 | Hayafuji et al. |
| 5,133,713 A | 7/1992 | Huang et al. |
| 5,133,726 A | 7/1992 | Ruiz et al. |
| 5,176,628 A | 1/1993 | Charles et al. |
| 5,201,749 A | 4/1993 | Sachse et al. |
| 5,207,683 A | 5/1993 | Goode et al. |
| 5,215,104 A | 6/1993 | Steinert |
| 5,217,459 A | 6/1993 | Kamerling |
| 5,226,910 A | 7/1993 | Kajiyama et al. |
| 5,242,404 A | 9/1993 | Conley et al. |
| 5,271,379 A | 12/1993 | Phan et al. |
| 5,273,406 A | 12/1993 | Feygin |

| | | |
|---|---|---|
| 5,273,524 A | 12/1993 | Fox et al. |
| 5,285,795 A | 2/1994 | Ryan et al. |
| 5,322,505 A | 6/1994 | Krause et al. |
| 5,330,470 A | 7/1994 | Hagen |
| 5,354,268 A | 10/1994 | Peterson et al. |
| 5,364,395 A | 11/1994 | West, Jr. |
| 5,374,188 A | 12/1994 | Frank et al. |
| 5,380,280 A | 1/1995 | Peterson |
| 5,383,454 A | 1/1995 | Bucholz |
| 5,395,368 A | 3/1995 | Ellman et al. |
| 5,403,276 A | 4/1995 | Schechter et al. |
| 5,403,311 A | 4/1995 | Abele et al. |
| 5,437,678 A | 8/1995 | Sorensen |
| 5,465,633 A | 11/1995 | Bernloehr |
| 5,474,532 A | 12/1995 | Steppe |
| 5,476,448 A | 12/1995 | Urich |
| 5,476,473 A | 12/1995 | Heckele |
| 5,496,339 A | 3/1996 | Koepnick |
| 5,507,751 A | 4/1996 | Goode et al. |
| 5,520,684 A | 5/1996 | Imran |
| 5,527,332 A | 6/1996 | Clement |
| 5,527,356 A | 6/1996 | Peyman et al. |
| 5,531,744 A | 7/1996 | Nardella et al. |
| 5,556,397 A | 9/1996 | Long et al. |
| 5,566,681 A | 10/1996 | Manwaring et al. |
| RE35,421 E | 1/1997 | Ruiz et al. |
| D377,524 S | 1/1997 | Lipp |
| 5,591,174 A * | 1/1997 | Clark et al. ............... 606/130 |
| 5,611,799 A | 3/1997 | Smith |
| 5,624,394 A | 4/1997 | Barnitz et al. |
| 5,643,304 A | 7/1997 | Schechter et al. |
| 5,693,013 A | 12/1997 | Geuder |
| 5,700,240 A | 12/1997 | Barwick, Jr. et al. |
| 5,704,927 A | 1/1998 | Gillette et al. |
| 5,738,677 A | 4/1998 | Colvard et al. |
| 5,779,723 A | 7/1998 | Schwind |
| 5,782,849 A | 7/1998 | Miller |
| 5,787,760 A | 8/1998 | Thorlakson |
| 5,795,328 A | 8/1998 | Barnitz et al. |
| 5,810,857 A * | 9/1998 | Mackool .................... 606/166 |
| 5,814,010 A | 9/1998 | Ziegler |
| 5,817,075 A | 10/1998 | Giungo |
| 5,868,728 A | 2/1999 | Giungo et al. |
| 5,916,330 A | 6/1999 | Jacobson |
| 5,941,250 A | 8/1999 | Aramant et al. |
| 5,944,731 A | 8/1999 | Hanna |
| 5,957,921 A | 9/1999 | Mirhashemi et al. |
| 5,989,272 A * | 11/1999 | Barron et al. ............... 606/161 |
| 6,013,049 A | 1/2000 | Rockley et al. |
| 6,019,754 A | 2/2000 | Kawesch |
| 6,045,563 A | 4/2000 | Duprat |
| 6,051,009 A * | 4/2000 | Hellenkamp et al. ....... 606/166 |
| 6,059,805 A | 5/2000 | Sugimura et al. |
| 6,083,236 A * | 7/2000 | Feingold ..................... 606/166 |
| 6,086,544 A | 7/2000 | Hibner et al. |
| 6,090,119 A * | 7/2000 | Pierce et al. .................. 604/22 |
| 6,139,560 A * | 10/2000 | Kremer ....................... 606/107 |
| 6,165,189 A * | 12/2000 | Ziemer ....................... 606/166 |
| 6,228,099 B1 * | 5/2001 | Dybbs ........................ 606/166 |
| RE37,304 E * | 7/2001 | Van Heugten et al. ...... 606/167 |
| 6,302,896 B1 * | 10/2001 | Carriazo et al. ............ 606/166 |
| 6,358,260 B1 * | 3/2002 | Ross et al. .................. 606/166 |
| 6,447,526 B1 * | 9/2002 | Carriazo ..................... 606/166 |

OTHER PUBLICATIONS

Storz Irrigation Aspiration System Product Brochure and Instruction Manual.
United Surgical Corporation Brochure on "Phacotron Plus", one page.
Surgical Design Company Brochure on Keates Ultrasonic I/E Mini Probe by A. Banko, 2 pages.
Surgical Design Corporation Brochure on U.S., Phaco System, 1 page.
Coopervision Brochure on System VI, 1 page.
Murayama et al. "A Portable Air Driving Unit for Blood Pumps", Japanese Journal of Artificial Organs, vol. 14, No. 3, pp. 1206–1209 (English Translation).
Scuderi, et al., French article entitled "La Chirurgie de la Cartaracte Congenitale", pp. 174–185. (English translation).
Hayashi et al., Japanese Experience with Ventricular Assist Devices IBEE Engineering in Medicine and Biology Magazine Mar. 1986, pp. 30–36.
Grieshaber and Co. of Siwtzerland, "Sutherland Rotatable Intraocular Microscissors", 2 pages.
JCERS and Tissue Removal Systems, Diskecter™ System, Rapid Tissue Removal System advertisement.
Charles and Wang, "A Linear Suction Control for the Vitreous Cutter (Ocutome)", Arch. Ophthalmol. vol. 99, Sep. 1981, p. 1631.
Crosby, "On Control of Artificial Hearts", pp. 89–114.
Mrava, Cardiac Engineering, vol. 3, pp. 31–68.

* cited by examiner

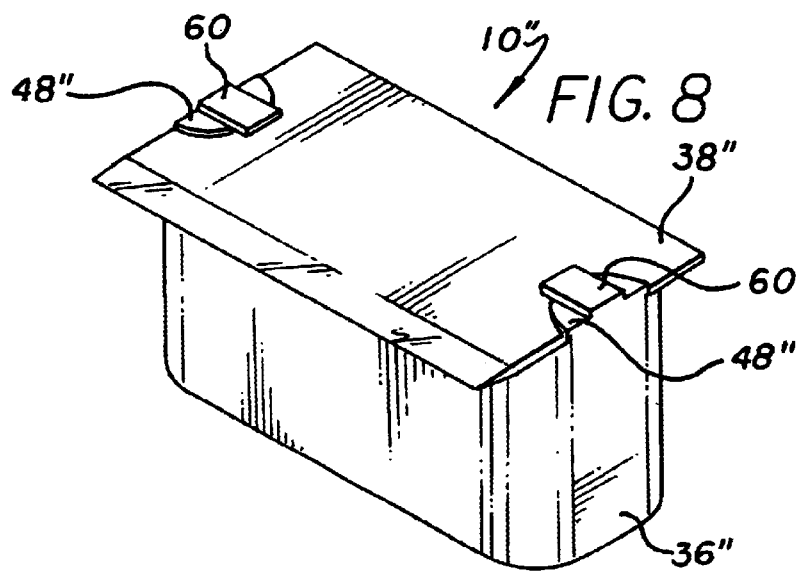
FIG. 8
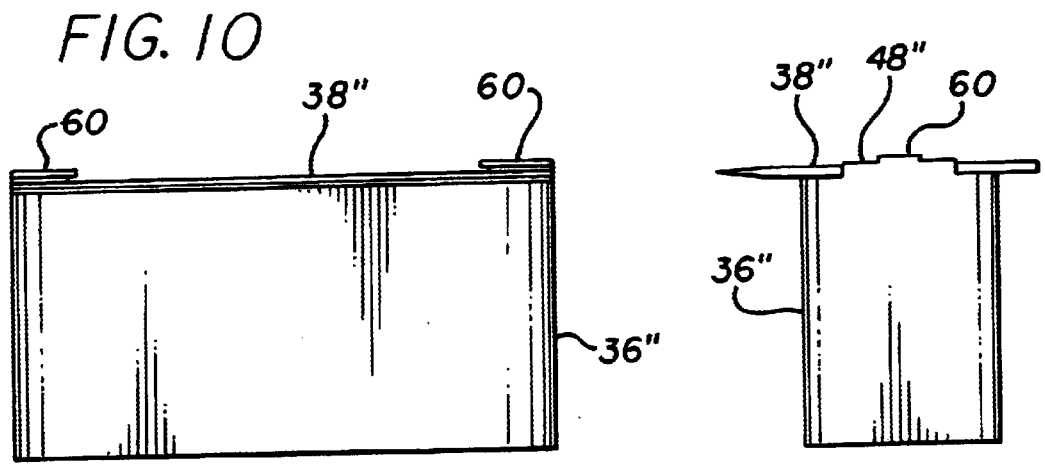
FIG. 10
FIG. 9
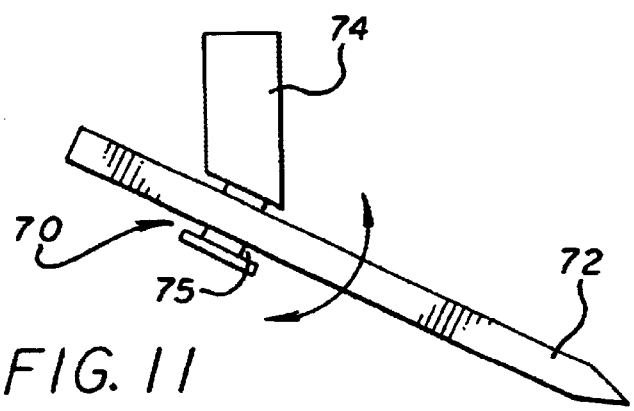
FIG. 11

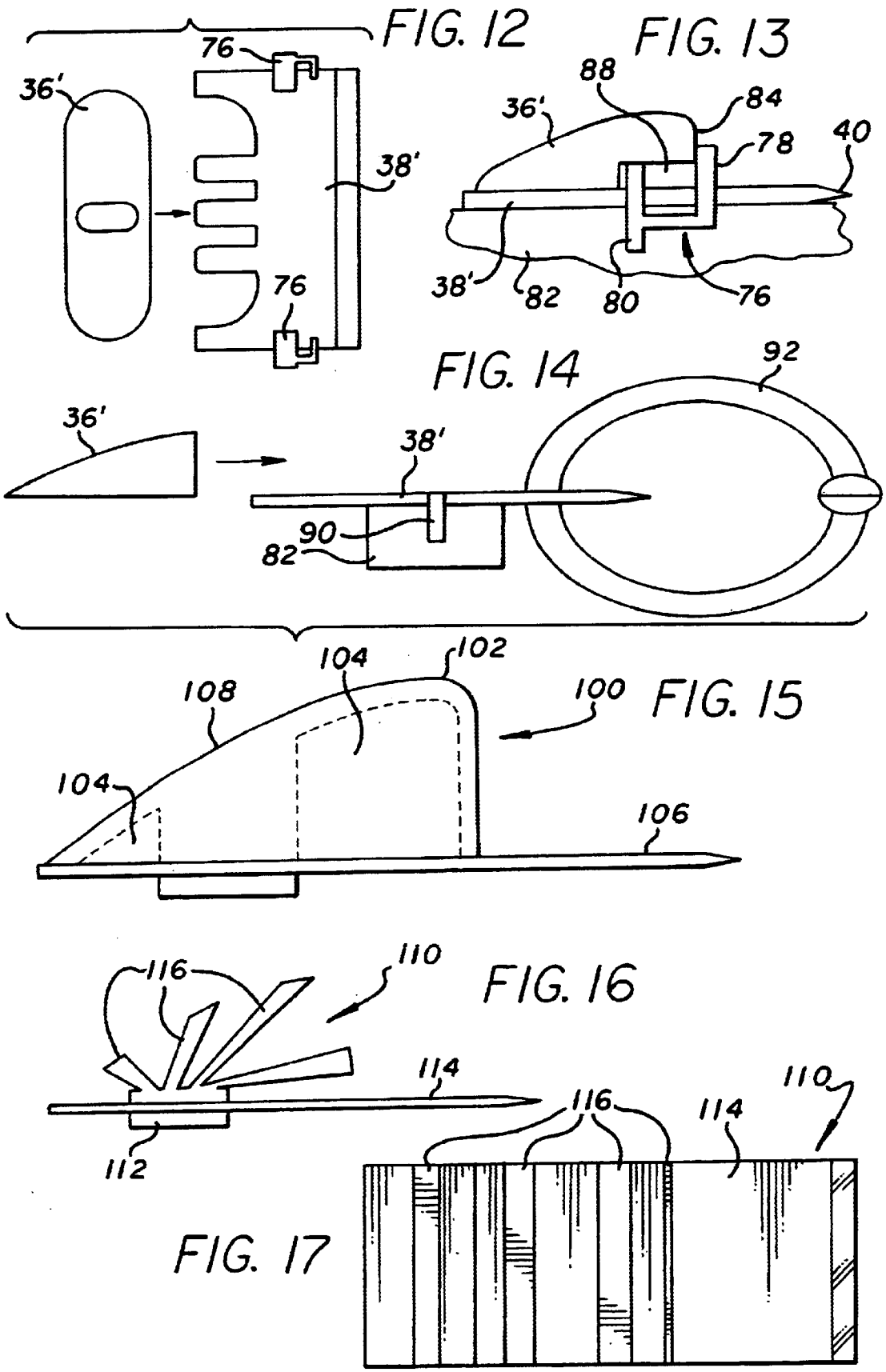

CUTTING BLADE ASSEMBLY FOR A MICROKERATOME

BACKGROUND OF THE INVENTION

1. Field of the Invention

The present invention relates to a blade assembly that can be assembled into a medical device that is used to cut a cornea.

2. Prior Art

There have been developed a number of different surgical techniques to correct hyperopic or myopic conditions of a human eye. U.S. Pat. No. 4,840,175 issued to Peyman discloses a procedure wherein a thin layer of the cornea tissue is cut and removed from the cornea. A laser beam is then directed onto the exposed corneal tissue in a predetermined pattern. The laser beam ablates corneal tissue and changes the curvature of the eye. This procedure is sometimes referred to as Laser in situ Keratomileusis (LASIK).

U.S. Pat. No. Re 35,421 issued to Ruiz et al. discloses a device for cutting a cornea in a LASIK procedure. Such a device is commonly referred to as a microkeratome. The Ruiz microkeratome includes a ring that is placed onto a cornea and a blade that is located within an opening of the ring. The device also contains a drive mechanism which moves the blade across the cornea in a first direction while the blade moves in a reciprocating transverse direction to cut the eye. The device can create a lamella flap of the cornea which is flipped back so that the stromal bed of the cornea can be ablated with a laser.

U.S. Pat. No. 6,051,009 issued to Hellenkamp et al. discloses a microkeratome that is sold under the trademark HANSATOME. The HANSATOME microkeratome moves the blade in an arcuate path about the cornea. The HANSATOME includes a disposable blade assembly that can be readily loaded and removed from the device. The blade assembly includes a blade holder that is attached to a cutting blade. The blade holder has a recess that receives the end of a drive shaft. Rotation of the output shaft both moves the blade in an arcuate path and moves the blade in a back and forth motion to create the lamella flap of the cornea.

It is critical to control the depth of the cut to prevent a deep or shallow cut of the cornea. The depth of the cut is a function of the distance between the cutting edge of the blade and a reference surface of the blade holder. The HANSATOME blade holder is attached to the cutting blade by a pair of plastic protrusions that extend from the blade holder through corresponding apertures of the blade. The plastic protrusions located on the underside of the blade holder are then ultrasonically welded to the top side of the blade. The accuracy of the distance between the cutting edge and the reference surface, and thus the depth of the cut into the cornea, is dependent upon the mechanical tolerance between the cutting edge and the aperture of the blade, and the mechanical tolerance between the protrusions and the reference surface of the blade holder. This tolerance "build up" can reduce the predictability of the cutting depth. It would be desirable to provide a blade assembly and process for assembling the blade assembly that would tightly control the tolerance between the cutting edge and the reference surface and thus the depth of the cut.

BRIEF SUMMARY OF THE INVENTION

One embodiment of the present invention is a blade assembly that can be assembled to a medical device used to cut a cornea. The blade assembly may include a blade holder that is coupled to a blade. The blade has a notch.

BRIEF DESCRIPTION OF THE DRAWINGS

FIG. 8 is a perspective view of another embodiment of a blade assembly;

FIG. 9 is a side view of the blade assembly shown in FIG. 8;

FIG. 10 is front view of the blade assembly shown in FIG. 8;

FIG. 11 is a side view of another embodiment of a blade assembly;

FIG. 12 is a top view showing a blade holder and a blade secured by a stabilizing post that is used to calibrate the holder;

FIG. 13 is a side view showing the blade holder assembled to the blade;

FIG. 14 is a top view showing a blade secured by a clamp that is used to calibrate the blade holder;

FIG. 15 is a side view of another embodiment of a blade assembly;

FIG. 16 is a side view of another embodiment of a blade assembly;

FIG. 17 is a top view of the blade assembly shown in FIG. 16.

DETAILED DESCRIPTION OF THE PREFERRED EMBODIMENTS

In general the present invention includes a blade assembly that can be assembled into a microkeratome which is used to cut a cornea. The blade assembly is constructed in a manner that minimizes the tolerance of the cutting depth into the cornea. The blade assembly includes a blade holder that can be pressed onto a blade. The relative position of the blade holder can be calibrated to control the distance between a reference surface of the blade holder and the cutting edge of the blade. This distance defines the cutting depth of the blade. The blade holder is coupled to the blade with an interference fit that both secures the holder while providing for calibration of the assembly.

Figure 1:
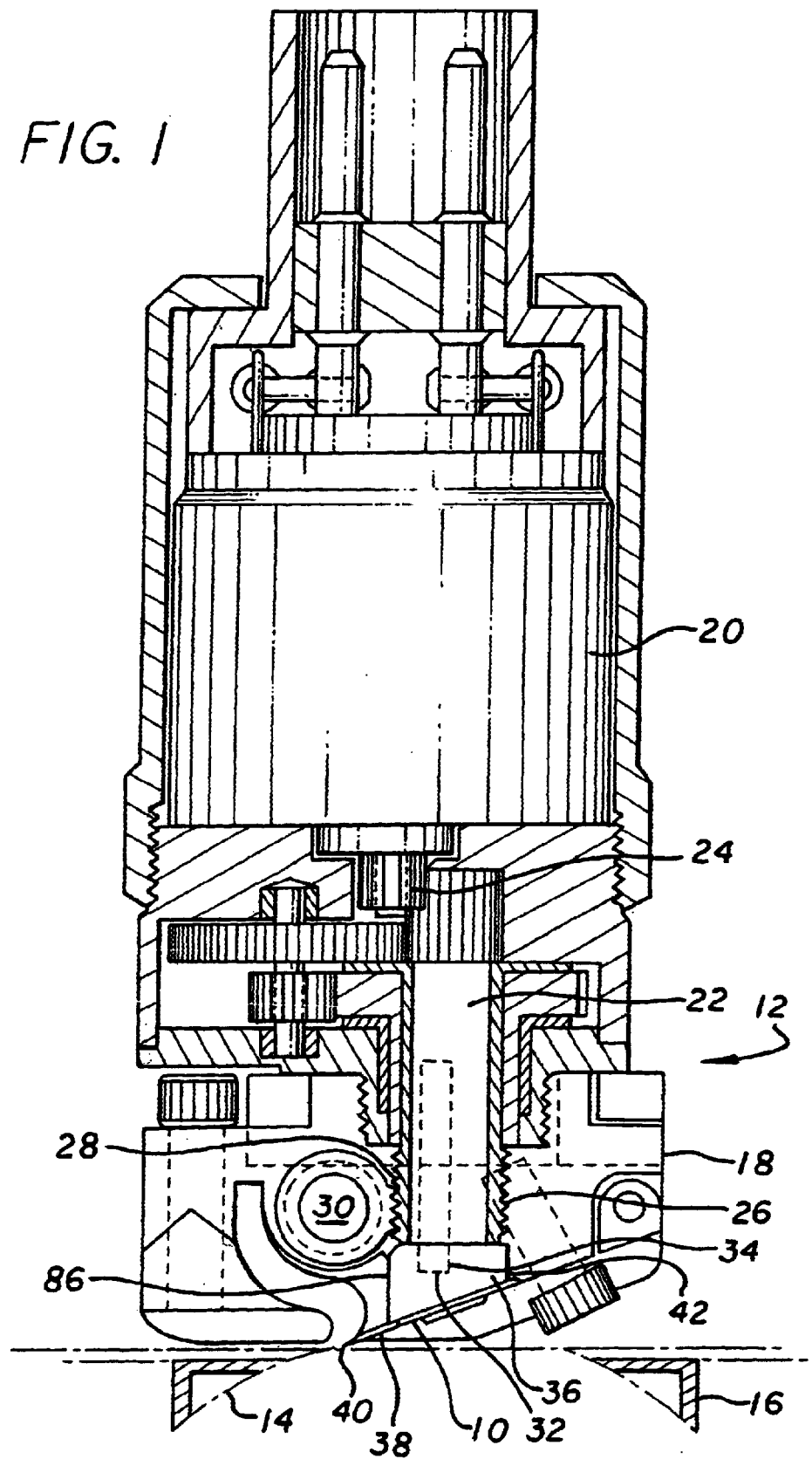
FIG. 1 is a side view of an embodiment of a microkeratome with a blade assembly of the present invention.

Referring to the drawings more particularly by reference numbers, FIG. 1 shows an embodiment of a blade assembly 10 assembled into a microkeratome 12. The microkeratome 12 is typically used to create a lamella in a cornea 14 as an initial step in a LASIK procedure. The microkeratome 12 may be the same or similar to the device disclosed in U.S. Pat. No. 6,051,009 issued to Hellenkamp et al., which is hereby incorporated by reference. The device disclosed in the '009 patent is also sold by Bausch & Lomb under the trademark HANSATOME. Although the HANSATOME is shown and described, it is to be understood that the blade assembly 10 of the present invention can be used in other microkeratomes.

The microkeratome 12 includes a ring 16 that is placed onto the cornea 14 and typically held in place by a vacuum pressure. The microkeratome 12 also includes a cutting head assembly 18 that is coupled to the ring 16. The cutting head assembly 18 includes a motor 20 that is coupled to an output shaft 22 by a gear assembly 24. The output shaft 22 has an external thread 26 that is coupled to a corresponding thread 28 of a drive shaft 30. The drive shaft 30 is coupled to a track (not shown) of the ring 16. Rotation of the output shaft 22, turns the drive shaft 30 and causes the entire cutting head assembly 18 to move about the cornea 14 along an arcuate path.

The output shaft 22 also has a pin 32 that extends into a corresponding slot 34 of a blade holder 36. The blade holder 36 is attached to a blade 38 which has a cutting edge 40 that cuts the cornea 14. Rotation of the output shaft 22 causes a reciprocating transverse movement of the blade 38. The reciprocating movement of the blade 38 cuts corneal tissue while the drive shaft 30 moves the entire assembly 18 across the cornea 14. The blade assembly 10 can be replaced by removing the assembly 10 from a blade cavity 42 of the cutting head assembly 18.

Figure 2:
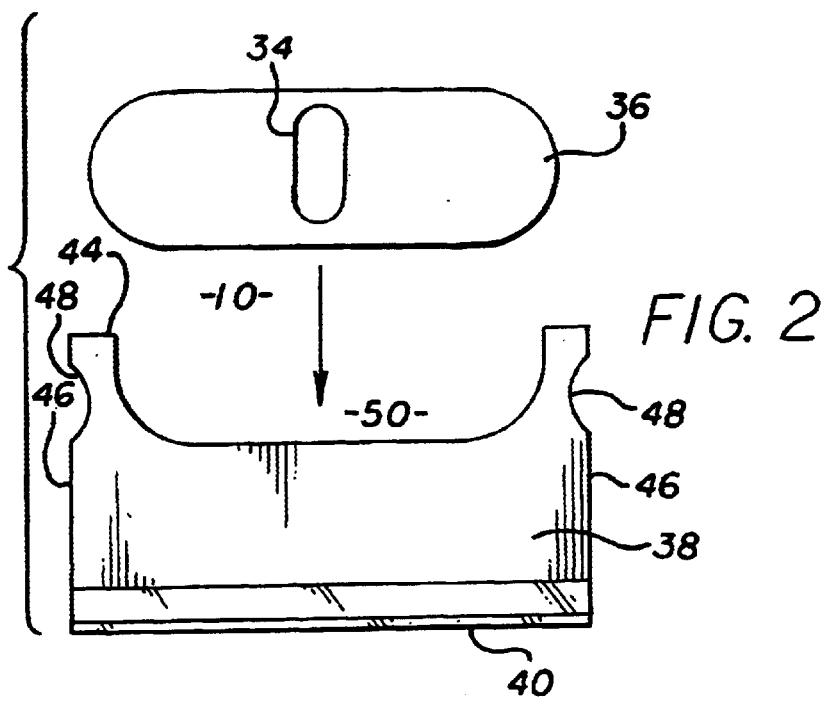
FIG. 2 is an exploded top view of an embodiment of a blade assembly.

FIG. 2 shows an embodiment of a blade assembly 10 that includes the blade holder 36 and a blade 38. The blade 38 is typically constructed from a hard stainless steel material that is stamped or machined into the configuration shown. The blade 38 may include the cutting edge 40, a rear edge 44 and a pair of side edges 46. The side edges 46 may each have a notch 48. The rear edge 44 may also have a notch 50.

The notches 48 may provide a feature that allows an operator to grab the blade assembly 10 and load the assembly 10 into the microkeratome 12. Additionally, a plurality of blades 38 may be loaded and transported on a rack (not shown) with pins that extend through the notches 48. The notches 48 may also provide reference surfaces for fixture alignment pins (not shown) used to align and calibrate the blade holder 36 with the blade 38.

Figure 3:
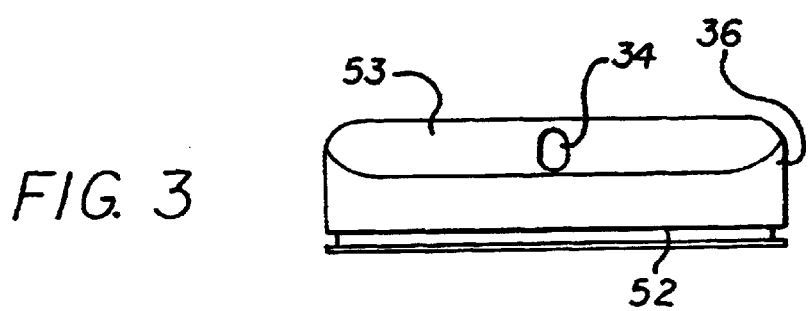
FIG. 3 is a front view of a blade holder of the blade assembly.

As shown in FIG. 3, the blade holder 36 may have an outer groove 52. The blade holder 36 may also have a tapered top surface 53 to provide clearance for the pin 32 when the assembly 10 is loaded into the microkeratome 12. The blade holder 36 may be constructed from a plastic material, wherein the groove 52 and slot 34 are either molded or machined into the holder 36. Referring to FIG. 2, the blade holder 36 can be assembled onto the blade 38 by pushing 36 the holder 36 into the notch 50, so that the edge of the notch 50 extends into the groove 52 of the side of the blade holder 36.

Figure 4:
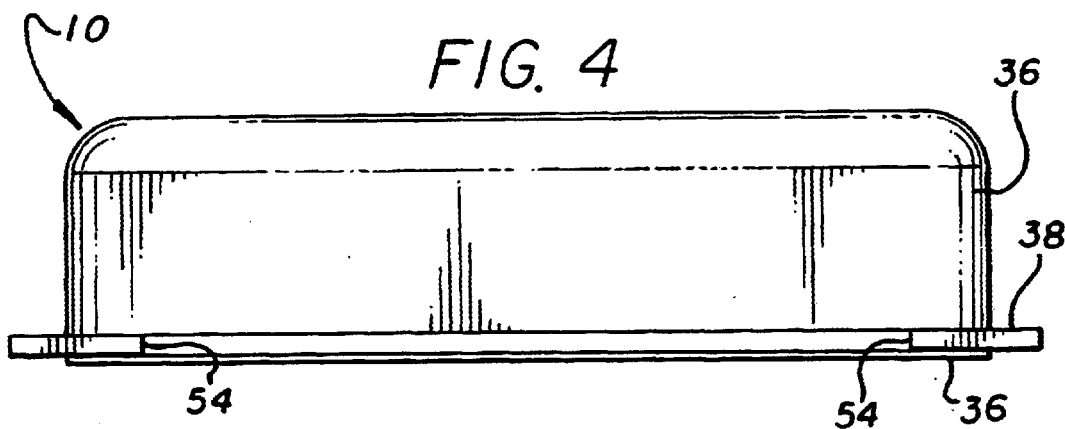
FIG. 4 is a side view of the blade assembly.

As shown in FIG. 4, the blade holder 36 engages the inner edges 54 of the blade notch 52. The blade holder 36 is held in place by frictional forces between the holder 36 and the edges 54 to create a frictional fit. The blade holder 36 may be further secured to the blade 38 by an adhesive or other means.

Figure 5:
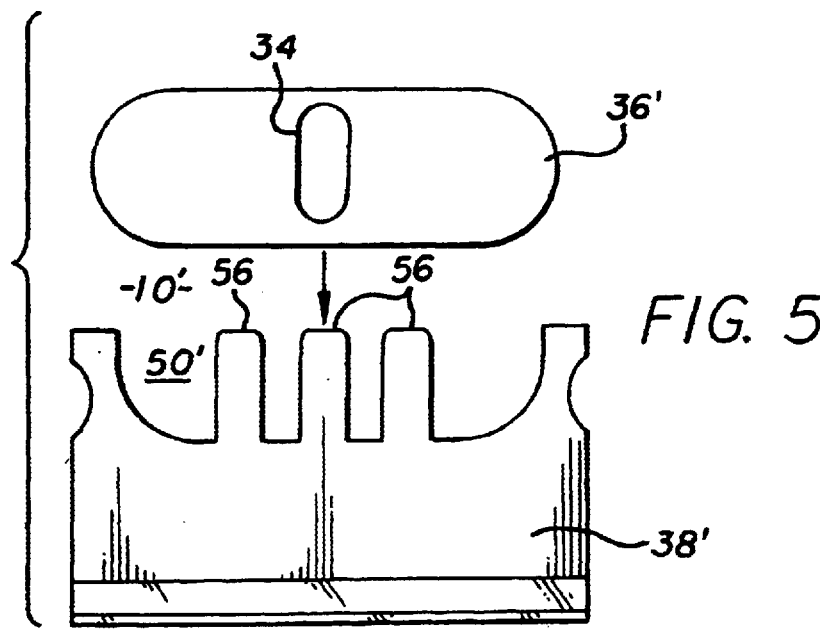
FIG. 5 is an exploded top view of another embodiment of a blade assembly.
Figure 6:
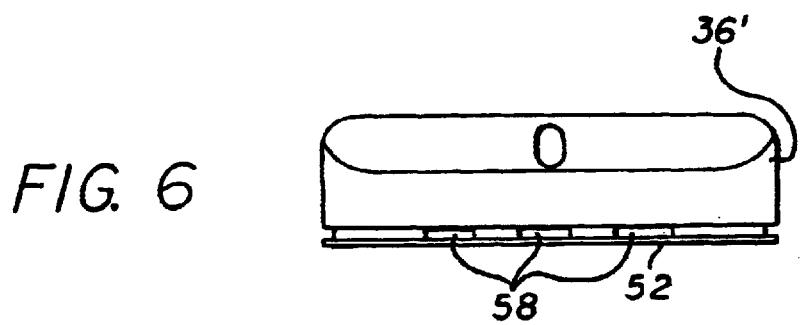
FIG. 6 is a side view of a blade holder of the assembly shown in FIG. 5.
Figure 7:
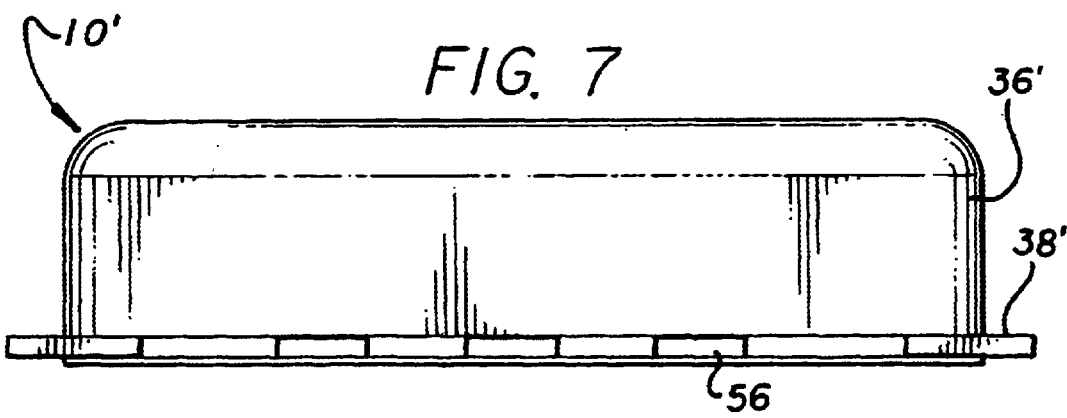
FIG. 7 is a side view of the blade assembly shown in FIG. 5.

FIGS. 5, 6 and 7 show another embodiment of a blade assembly 10'. In this embodiment, the blade 38' has a plurality of fingers 56 within the notch 50'. The fingers 56 can extend into corresponding slots 58 of the blade holder 36'. The fingers 56 increase the surface area and corresponding frictional forces that couple the blade 38' to the blade holder 36'.

FIGS. 8, 9 and 10 show yet another embodiment of a blade assembly 10". The blade holder 36" of the assembly 10" has a pair of clips 60 that secure the holder 36" to the blade 38" within blade notches 48". The clips 60 secure the holder 36" to the blade 38" with frictional forces. With this embodiment the blade holder 36" can move relative to the blade 38" during installation into the microkeratome 12. The relative movement provides a mechanical float feature that compensates for tolerances in the cutting head assembly 18, particularly the cavity 42 of the microkeratome.

FIG. 11 shows another embodiment of a blade holder assembly 70 wherein a blade 72 can pivot relative to the blade holder 74 as indicated by the arrow. This embodiment provides a mechanical float that will compensate for tolerances in the assembly 20 and the microkeratome 12. The float is created by a gap 75 between the blade holder 74 and the blade 72. The blade holder 74 may be held in place by frictional forces between an inner edge of the holder 74 and an outer edge of the blade 72.

FIGS. 12 and 13 show a method for assembling and calibrating the blade holder 36' to the blade 38'. The blade 38' may be held in place by a pair of stabilizer posts 76. The posts 76 extend through the notches 48 of the blade 38. Each stabilizer post 76 includes a stop 78 that is connected to a pin 80. Each pin 80 is attached to a fixture plate 82.

The blade holder 36' is pushed onto the blade 38' until a reference surface 84 of the holder 36' abuts against the stop 78. The reference surface 84 rest against a corresponding reference surface 86 of the cutting head assembly 18 shown in FIG. 1. The stop 78 provides a datum point that closely controls the distance between the, reference surface 84 and the cutting edge 40 of the blade 38. The distance between the reference surface 84 and the cutting edge 40 defines the cutting depth of the blade 38'. The blade holder 36' may have a pair of outer notches 88 that provide a clearance for the pins 80 when the holder 36' is pushed onto the blade '38.

FIG. 14 shows another means for assembling and calibrating the blade holder 36' to the blade 38'. The blade 38' can be secured to a fixture plate 82 by a couple of pins 90 that extend into the blade notches. A clamp 92 is then coupled to the blade 38. The blade holder 36' is pushed onto the blade 38' until the reference surface 84 abuts against the clamp 92. The distance between the clamp 88 and the cutting edge 40 can be accurately controlled to minimize the tolerance between the reference surface 84 and the edge 40.

FIG. 15 shows another embodiment of a blade assembly 100 that includes a blade holder 102 which has one or more cavities 104. The blade holder 102 is coupled to a blade 106 by any of the embodiments shown in FIGS. 2–11. The cavities 104 reduce the stiffness of the blade holder 104 so that the holder 104 can be more readily installed into an undersized blade cavity 42. Additionally, a tool (not shown) can be inserted in a cavity 104 and used to push the blade holder 102 onto the blade 102. The blade holder 102 may also have a contoured top surface 108 that reduces the surface area in contact with the cutting head assembly 18. The contoured surface 108 reduces the tolerance requirements of the holder 102 and the cavity 42.

FIGS. 16 and 17 show another embodiment of a blade assembly 110 that includes a blade holder 112 coupled to a blade 114. The blade holder 112 can be attached to the blade 114 by an interference fit as described in FIGS. 2–11. The blade holder 112 includes a plurality of fingers 116. The fingers 116 provide a means to grasp the assembly 110. The individual fingers 116 also minimize the friction and lack of fit with the blade cavity 42. The most distal finger 116 provides a reference surface that abuts against the corresponding reference surface of the cavity 42.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

For example, although the blade assembly 10 shown in FIG. 2 shows a notch 50 in the blade 38, the assembly 10 could be constructed to eliminate the notch 50 and form a deep groove within the blade holder 36', essentially a mirror image of the embodiment shown.

What is claimed is:

1. A method for constructing a blade assembly that is placed into an inner cavity of a microkeratome, comprising:

pressing a front reference surface of a blade holder onto a rear edge of a blade from a rearward direction until the front reference surface reaches a desired distance from a front cutting edge, the blade holder having a slot that receives a pin of the microkeratome.

2. The method of claim 1, wherein the blade is placed into a stop.

3. The method of claim 1, wherein the blade is placed into a clamp.

4. A method for controlling a distance between a cutting edge of a blade and a reference surface of a blade holder, wherein the blade and blade holder can be placed into an inner cavity of a microkeratome, comprising:

moving a blade holder onto a rear edge of a blade from a rearward direction until a front reference surface of the blade holder engages a tool, the tool provides a datum for the distance between the cutting edge and the reference surface of the blade holder, the blade holder having a slot that receives a pin of the microkeratome.

5. The method of claim 4, wherein the tool is a stop pin.

6. The method of claim 5, wherein the tool is a clamp.

* * * * *